United States Patent
Arling

[19]

[11] Patent Number: 5,872,571
[45] Date of Patent: *Feb. 16, 1999

[54] METHOD AND APPARATUS FOR DISPLAY OF MULTI-PLANAR ULTRASOUND IMAGES EMPLOYING IMAGE PROJECTION TECHNIQUES

[75] Inventor: Robert S. Arling, North Andover, Mass.

[73] Assignee: Hewlett-Packard Company, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 647,518

[22] Filed: May 14, 1996

[51] Int. Cl.$^6$ ..................................................... G06T 17/00
[52] U.S. Cl. ............................................ 345/427; 345/420
[58] Field of Search .................................. 395/125–193; 345/419–433; 600/443

[56] References Cited

U.S. PATENT DOCUMENTS

| | | | |
|---|---|---|---|
| 4,719,585 | 1/1988 | Cline et al. ............................... | 345/424 |
| 4,727,365 | 2/1988 | Bunker et al. ........................... | 340/728 |
| 5,315,999 | 5/1994 | Kinicki et al. ........................... | 600/443 |
| 5,467,779 | 11/1995 | Smith et al. ......................... | 128/660.1 |

OTHER PUBLICATIONS

IEEE Transactions On Biomedical Engineering, vol. BME–30, No. 8, Aug. 1983.

*Primary Examiner*—Almis R. Jankus

[57] ABSTRACT

An ultrasound imaging method employs an ultrasound transducer which outputs a beam that is scanned along a scan plane. The transducer is controllable to move the scan plane to plural non-coplanar orientations. The imaging method comprises the steps of: operating the ultrasound transducer to acquire and store data indicative of an ultrasound image in each of a plurality of scan planes that are non-coplanar. For each ultrasound image that is acquired in a scan plane that is non-coplanar with a reference scan plane, the ultrasound image is transformed by performing a projection of the non-coplanar scan plane and its image data onto the reference scan plane. The projected non-coplanar ultrasound image is then displayed by employing the projection data indicative of the image.

11 Claims, 2 Drawing Sheets

METHOD AND APPARATUS FOR DISPLAY
OF MULTI-PLANAR ULTRASOUND IMAGES
EMPLOYING IMAGE PROJECTION
TECHNIQUES

FIELD OF THE INVENTION

This invention relates to the display of ultrasound images and, more particularly, to a quasi-three dimensional display of ultrasound images acquired during image scans in non-coplanar image planes.

BACKGROUND OF THE INVENTION

Many modern ultrasound systems employ phased array transducers which comprise a number of individual transducers that are arranged, side by side, in a unitary assembly. In effect, the phased array of transducers acts like an acoustic lens with an electronically variable focal length. Such a phased array transducer, while stationary, is electronically controllable to steer and focus an ultrasound beam so as to achieve a B scan image.

B or brightness mode scanning is the most common type of ultrasound imaging. A B scan is a view of a cross-sectional slice through the object being imaged. A narrow pencil beam of ultrasound energy is swept through a scan sector to define a scan plane. The beam is formed from bursts of ultrasound and the repetition rate of the ultrasound pulse generation is selected so that the transmitted pulse has time to travel to the deepest target and back again before the next pulse is launched. The echoes vary in intensity according to the type of tissue or body structure causing the echoes. The echo return data is presented on a display in which the brightness depends upon the echo strength.

In addition to a phased array being able to provide an image in a single scan plane, certain phased array transducers are rotatable about an axis that is orthogonal to the transducer's emitting face. The rotation of the phased array structure enables the scan plane to be rotated about the orthogonal axis and thus enables multiple images to be acquired at various rotated scan plane orientations.

In addition to phased array ultrasound transducers, other types of ultrasound probes also are adapted to generate multiple image planes, I. e., "wobbler" probes, tomographic-type probes which produce multiple parallel planes at known spatial intervals, etc. Each of the abovementioned probes enables acquisition of more than one, two-dimensional ultrasound image without requiring a physical movement of the entire probe housing.

Ultrasound scanners typically display a two dimensional B scan image as a sector (or other geometrical shape) on a display screen. Although the image data within the sector changes as the transducer is moved and different areas of tissue are scanned, the sector shape, itself, remains constant regardless of transducer orientation. Further, when the scan plane of a rotatable phased array ultrasound probe is changed, the prior art display presents an identical sector scan as for all other scan planes.

A further indicator is sometimes provided on the display which informs the operator of the angular sensor position with respect to the tip of the ultrasound transducer. Such indicator may be an angle icon. The user is then forced to conceptualize the orientation of the scan plane in three-dimensional space and, in particular, in a three-dimensional position that is relative to other image planes acquired at the same probe tip position, but using different sensor angles. Such visualization on the part of the user requires substantial training and is still subject to error if, for any reason, the user is distracted during the ultrasound examination.

Thus, there is a need for an improved imaging method for multiplanar ultrasound images which enables the user to better visualize three dimensional objects that are scanned using multiple non-coplanar scan planes. There is further need for an improved ultrasound imaging method which enables a quasi-three dimensional viewing of scan planes that are non-coincident with a reference scan plane.

SUMMARY OF THE INVENTION

An ultrasound imaging method employs an ultrasound transducer which outputs a beam that is scanned along a scan plane. The transducer is controllable to move the scan plane to plural non-coplanar orientations. The imaging method comprises the steps of: operating the ultrasound transducer to acquire and store data indicative of an ultrasound image in each of a plurality of scan planes that are non-coplanar. For each ultrasound image that is acquired in a scan plane that is non-coplanar with a reference scan plane, the ultrasound image is transformed by performing a projection of the non-coplanar scan plane and its image data onto the reference scan plane. The projected non-coplanar ultrasound image is then displayed by employing the projection data indicative of the image.

DETAILED DESCRIPTION OF A PREFERRED EMBODIMENT

Figure 1:
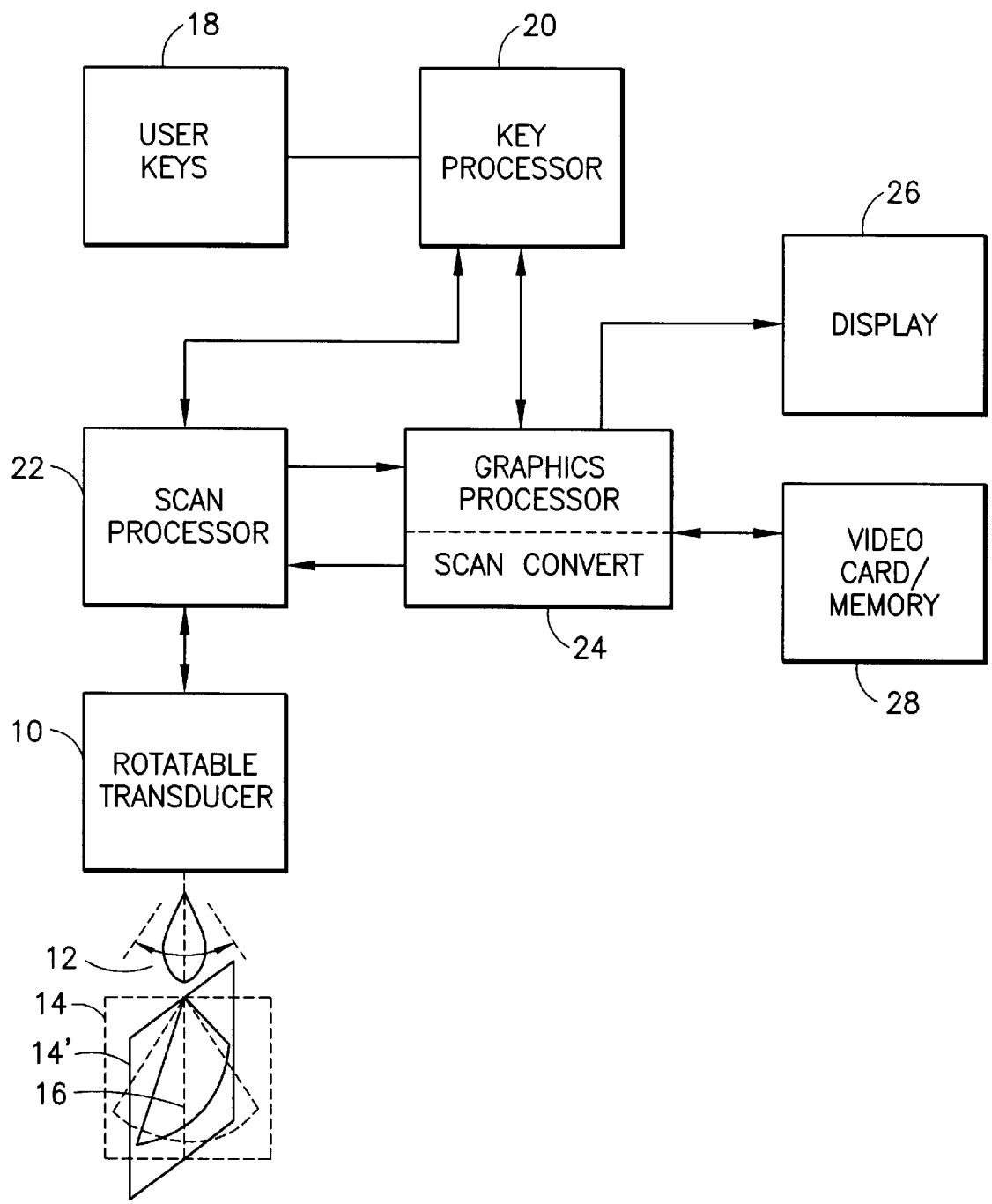
FIG. 1 is a block diagram of an ultrasound system embodying in the invention.

FIG. 1 illustrates a high level block diagram of an ultrasound system embodying the invention. A rotatable array transducer generates a beam 12 that is scanned in a planar scan plane 14. As transducer 10 is rotatable, scan plane 14 is also rotatable about axis 16 to a plurality of angular orientations (e.g., see scan plane 14'). Within each scan plane, beam 12 is swept in a pie-shaped manner (or other geometric shape scan) to interrogate a body positioned beneath transducer 10.

Overall control of transducer 10 is exercised by a user entering inputs via user keys 18 to a key processor 20. A scan processor 22, in response to inputs from key processor 20, controls the position of beam 12. Scan processor 22 provides control signals to transducer 10 to cause a scan movement of beam 12 and further receives the raw ultrasound data from transducer 10 and performs initial processing thereof.

Further controls enable rotation of the emitting face of transducer 10 to one of a plurality of scan planes 14, 14', etc. Outputs from key processor 20 are also fed to a graphics processor 24 which acts as a main controller for a connected display 26 and a video card/memory 28. Graphics processor includes a scan convert function which converts ultrasound data from scan processor 22 into a raster format, in which form the image is fed to video card/memory 28 for storage.

As will be hereafter understood, through appropriate user inputs via user keys 18 and key processor 20, display 26 is controlled to not only display ultrasound images from each of scan planes 14, 14', etc., but is further adapted to display an ultrasound image derived in one scan plane (e.g., 14'), as it is projected on a reference scan plane, e.g., scan plane 14.

In such manner, display 26 is able to indicate on its screen, a view of an ultrasound image scan plane, both from the vantage point where the scan plane is "parallel" to the plane of the display screen, and also when the scan plane is "positioned" at an angle to the display screen. In such manner, a quasi-3D image is displayed which assists the user in understanding the full context of each ultrasound image.

Figure 2:
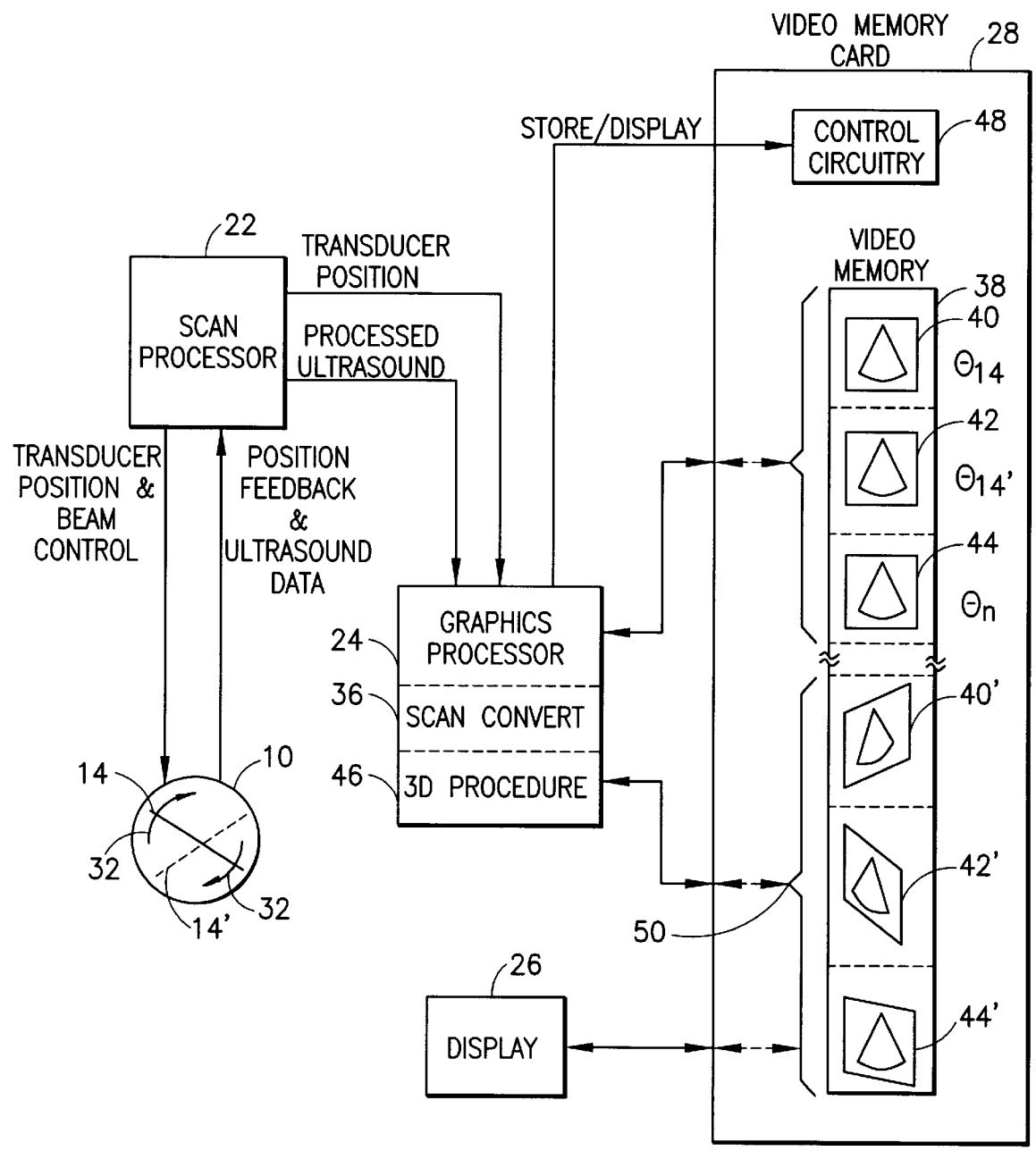
FIG. 2 is a further schematic diagram of the ultrasound system of FIG. 1, helpful in understanding the operation of the system of FIG. 1.

In FIG. 2, modules that are identical to those shown in FIG. 1 are numbered identically. In FIG. 2, however, rotatable transducer 10 is shown in a schematic plan view, with arrows 32 indicating the rotational capability of the transducer elements to enable a rotation of the angular orientation of the image scan plane. During a scan action, the raw ultrasound data is fed from transducer 10 into scan processor 22 where, after processing, it is fed to scan convert function 36 in graphics processor 24. The output of scan convert function 36 is a raster image of the ultrasound echo returns in the respective scan plane.

In essence, the output image data is organized such that, upon being viewed on a display screen, its presentation is as though it is being projected (and the user is positioned) at an angle which is orthogonal to the surface of the scan plane. Thus, each scan plane image output from scan convert function 36 appears identical in terms of its planar presentation on the screen of display 26, except that each succeeding image is, or may be, acquired at a different scan angle θ. Each scan plane image output from scan convert function 36 is stored in a video memory 38. Thus, scan plane images 40, 42, 44, etc. are stored in video memory 38 in the aforementioned orthogonal format that is well-known to those skilled in the art. Scan plane image 40 is the image derived along image plane 14, scan plane image 42 is the image derived along scan plane 14' and scan plane image 44 is the image derived along another scan plane "n".

To thereafter enable a quasi three-dimensional presentation of each of scan plane images 40, 42, 44, etc., graphics processor 24, in response to a user input, institutes a 3D procedure 46 by passing a control signal to control circuit 48. Control circuit 48 causes, for instance, scan plane image 40 to be accessed and passed to graphics processor 24 where the image data is subjected to an angular transform procedure. In specific, a reference scan plane is established which is "logically" parallel to the screen of display 26. An angular offset between scan plane image 40 and the reference scan plane is determined and the image data from scan plane 40 is subjected to a transform which projects the image onto the reference scan plane.

More specifically, scan plane 40, for instance, is accessed and each pixel at each address therein is transformed to a new x, y coordinate, based upon a geometric transformation. The geometric transformation is dependent upon the angular difference between the reference plane and scan plane image 40. The transform can also both scale and translate the image, if desired, but the principal action is to cause the individual pixels of scan plane image 40 to be projected onto the reference plane as though scan plane image 40 was being viewed through the reference plane at an azimuth that is perpendicular to the reference plane.

After being subjected to the transformation, the resultant projected scan plane image is stored in a further section of video memory 38, i.e., section 50. Thus, for instance, scan plane image 40' corresponds to a projected scan plane image 40. Similarly, scan plane images 42' and 44' correspond to projected scan plane images 42 and 44 (i.e., after being subjected to the transformation action).

Thereafter, graphics processor 24, via inputs to control circuitry 48, causes selective readout of the projected scan plane images, either singly or in serial fashion to provide a quasi-3D image showing. Further, graphics processor 24 can combine each of projected images 40', 42', 44', etc. into a single scan plane image. A hidden surface removal procedure can then be employed to allow only those pixels which are visible in the single scan plane to be displayed. Hidden surface removal is well known in the image processing art and requires no detailed description here.

As a result of the above indicated display action, each ultrasound image can be shown in various angular orientations, as viewed from the plane of the display screen, with the projected views giving visual cues to the user as to the position of each scan plane in relation to the reference scan plane. This display mode can be utilized to display 2D images in quasi 3D format, in real time. Further, by choosing which frames of data from a stored multi-frame image to display, a loop can be projected, with the projected data depicting slices of either a static object or a moving object—thereby giving a "real time" three-dimensional, time lapse image.

The imaging procedure further aids the user in transducer placement. By sweeping the scan plane of the transducer from 0° to 180°, while displaying image data in the quasi 3D mode, the user can more easily visualize exactly where the transducer tip is positioned relative to important anatomical features. It furthers provides a valuable training aid for the user, as it images relative spatial relationships in a manner which are easily recognizable.

While the above display procedure has been described in the context of a rotatable scan plane, the procedure is equally applicable to other non-rotational multi-plane probes and imaging modalities. Further, the invention is equally applicable to a phased array that is electronically scanable in plural dimensions. Additional processing, besides simple trigonometric projection, can be accomplished when displaying the projected image plane. Such processing may include perspective projection, depth cuing (making more "distant" parts of the sector, or other geometric shape, dimmer); and modification of the "lighting" of various portions of the image. Finally, while the invention has been described in the preferred embodiment using a scan converter to derive conventional images, which images are further processed to create projected image, it should be appreciated that the scan converter could be modified to directly produce the projected images.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

I claim:

1. An ultrasound imaging method employing an ultrasound transducer having an emitting face which outputs a beam that is scanable along a scan plane, the transducer controllable to move said scan plane to plural, intersecting, non-coplanar scan plane orientations, said method comprising the steps of:

operating said ultrasound transducer to acquire and store data indicative of a two-dimensional ultrasound image in each of said plural, intersecting, non-coplanar scan plane orientations;

for each ultrasound image acquired in a scan plane that is intersecting and non co-planar with a reference plane, transforming said ultrasound image by performing a projection of non-coplanar, two-dimensional scan plane data onto said reference plane to derive projection data indicative of said ultrasound image, as viewed from said reference plane; and displaying each said two-dimensional non-coplanar ultrasound image, either separately or in combination, by employing said projection data indicative of each said image.

2. The ultrasound imaging method as recited in claim 1, wherein said ultrasound transducer outputs a beam that is scanned along a scan plane that is orthogonal to the emitting face of said transducer, and said transducer is controllable to rotate said scan plane about an axis orthogonal to said emitting surface to plural non-coplanar scan planes.

3. The ultrasound imaging method as recited in claim 1, wherein said displaying step concurrently displays plural non-coplanar images.

4. The ultrasound imaging method as recited in claim 1, wherein said transforming step further maps data comprising multiple non-coplanar images onto said reference plane to create quasi-3D image data and said displaying step displays a quasi-3D image in accord with said quasi-3D image data.

5. The ultrasound imaging method as recited in claim 4, wherein said transforming step further performs a hidden surface removal action in arriving at said quasi-3D image data.

6. An ultrasound imaging system comprising:

ultrasound transducer means for outputting a beam that is scanned along a scan plane;

means for controlling said transducer to move said scan plane to plural, intersecting, non-coplanar scan plane orientations;

control means for operating said ultrasound transducer to acquire and store data indicative of a two-dimensional ultrasound image in each of said plural, intersecting, non-coplanar scan plane orientations;

processor means for performing a projection of each two-dimensional ultrasound image acquired in a scan plane that is intersecting and non co-planar with a reference plane, onto said reference plane to derive and store projection data indicative of said ultrasound image, as viewed from said reference plane; and display means for displaying each said two-dimensional ultrasound image, either separately or in combination, by employing said projection data indicative of each said image.

7. The ultrasound imaging system as recited in claim 6, wherein said ultrasound transducer means outputs a beam that is scanned along a scan plane that is orthogonal to an emitting face of said ultrasound transducer, and said ultrasound transducer is controllable to rotate said scan plane about an axis orthogonal to said emitting surface, to plural non-coplanar scan planes.

8. The ultrasound imaging system as recited in claim 6, wherein said processor means further maps data comprising multiple non-coplanar images onto said reference plane to create quasi-3D image data and causes said display means to display a quasi-3D image in accord with said quasi-3D image data.

9. The ultrasound imaging system as recited in claim 8, wherein said processor means further performs a hidden surface removal action in arriving at said quasi-3D image data.

10. The ultrasound imaging system as recited in claim 6, wherein said ultrasound transducer means comprises a phased array of transducers that are electronically scanable in at least one dimension.

11. The ultrasound imaging system as recited in claim 6, wherein said ultrasound transducer means comprises a phased array of transducers that are electronically scanable in plural dimensions.

* * * * *